(12) United States Patent
Frey et al.

(10) Patent No.: US 9,085,499 B2
(45) Date of Patent: *Jul. 21, 2015

(54) ENERGY EFFICIENCY IN ADSORPTIVE SEPARATION

(75) Inventors: Stanley J. Frey, Palatine, IL (US); Lewis H. Pettengill, Des Plaines, IL (US); Michael R. Van de Cotte, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 30 days.

This patent is subject to a terminal disclaimer.

(21) Appl. No.: 13/292,713

(22) Filed: Nov. 9, 2011

(65) Prior Publication Data

US 2013/0116495 A1    May 9, 2013

(51) Int. Cl.
C07C 7/12    (2006.01)

(52) U.S. Cl.
CPC .......................................... *C07C 7/12* (2013.01)

(58) Field of Classification Search
None
See application file for complete search history.

(56) References Cited

U.S. PATENT DOCUMENTS

| | | | |
|---|---|---|---|
| 2,820,070 A | | 1/1958 | Bennett et al. |
| 5,470,464 A | * | 11/1995 | Priegnitz ..................... 210/198.2 |
| 5,565,104 A | | 10/1996 | Priegnitz |
| 5,595,665 A | | 1/1997 | Noe |
| 5,685,992 A | | 11/1997 | Cohen et al. |
| 5,770,088 A | | 6/1998 | Ikeda et al. |
| 6,348,637 B1 | | 2/2002 | Harris |
| 6,395,951 B1 | | 5/2002 | Hamm |
| 7,208,651 B2 | | 4/2007 | Frey |
| 7,899,654 B2 | * | 3/2011 | Zhang et al. ........................ 703/2 |
| 2006/0273013 A1 | * | 12/2006 | Chin et al. ..................... 210/656 |
| 2009/0047190 A1 | | 2/2009 | Zhou |
| 2010/0264063 A1 | * | 10/2010 | Vercoe ............................ 208/44 |
| 2011/0077448 A1 | | 3/2011 | Frey |

FOREIGN PATENT DOCUMENTS

| | | |
|---|---|---|
| FR | 2743068 A1 | 7/1997 |
| WO | 9907656 A2 | 2/1999 |

OTHER PUBLICATIONS

Dupraz, "New Production Processes for High-Purity Paraxylene", Hydrocarbon Technology International (ISSN 0952-1399) 57-59,62-64 (1998).
Poon, "Ways in Which Valve Controllers Improve Paraxylene Processes", Hydrocarbon Asia, Nov./Dec. 2007, p. 42-46.
Kasatkin, Main Process and Apparatus of Chemical Engineering, 7th Ed., Moscow, 1961, p. 90, par. 1, p. 110-111.
PCT International Search Report and Written Opinion dated Dec. 13, 2012 for PCT/US2012/056475, Applicant's file reference H0025047.

* cited by examiner

*Primary Examiner* — Tam M Nguyen

(57) ABSTRACT

The present process comprises a means for energy savings in one or more process pumps by driving the one or more pumps with a variable-speed driving means. The invention is particularly useful in the separation of an adsorbed product from a mixture of components using simulated-moving-bed adsorption associated with a large circulating stream pumped with variable-speed driving means for conservation of energy relative to the known art. The improvement is particularly applicable to a process for the separation of para-xylene from mixed $C_8$ aromatics.

18 Claims, 3 Drawing Sheets

ENERGY EFFICIENCY IN ADSORPTIVE SEPARATION

FIELD OF THE INVENTION

The subject invention relates to energy conservation in processes requiring substantial energy requirements for pumping liquids. More specifically, the invention relates to energy conservation in processes for the adsorptive separation of hydrocarbons.

BACKGROUND OF THE INVENTION

The present invention is applied in the context of petroleum and petrochemical processes wherein substantial energy is consumed in the pumping of liquids. Examples of such applications are the pumping of liquid feeds to elevated pressures and recycle processes in which relatively large volumes of liquids are circulated within the process. The invention is relevant wherein the pumping rate is variable, with resulting inefficiency in the energy requirement, and is particularly relevant when turndown in an important consideration.

One specific application is in continuous-separation processes for the selective adsorption of an extract from a mixture comprising a raffinate and/or another byproduct. Such processes are in widespread use for the separation of hydrocarbons, for example the separation of para-xylene and/or meta-xylene from a mixture of $C_8$ aromatics, normal paraffins from a paraffin mixture, or specific olefins from a mixture of olefins and paraffins. Generally, the processes use a solid adsorbent which preferentially retains the extract in order to separate the extract from the rest of the mixture.

The solid adsorbent often is in the form of a simulated moving bed, wherein the bed of solid adsorbent is held stationary and the locations at which the various streams enter and leave the bed are periodically moved. The adsorbent bed itself is usually a succession of fixed sub-beds. The shift in the locations of liquid input and output in the direction of the fluid flow through the bed simulates the movement of the solid adsorbent in the opposite direction. The shift in locations of liquid input and output is accomplished by a fluid directing device known generally as a rotary valve which works in conjunction with distributors located between the adsorbent sub-beds. A pumparound stream is conducted by pumps circulating liquid from the bottom to the top of the bed of adsorbent. The composition and volume of the pumparound stream at a given location changes with each valve step. The bed of adsorbent may be contained in two or more chambers, with corresponding numbers of pumparound streams and pumps and two pumps being typical in such adsorption units. The pumparound pumps, moving substantial and varying quantities of material around one or multiple adsorbent chambers, are significant energy consumers.

For greater detail regarding the simulated moving bed and its operation, see U.S. Pat. No. 2,985,589. Relevant to a para-xylene separation process; see Mowry, J. R. In Handbook of Petroleum Refining Processes; Meyers, R. A. Ed.; McGraw-Hill: New York, 1986; pp 8-79 to 8-99.

SUMMARY OF THE INVENTION

The purpose of the present invention is to provide energy savings in variable-rate pumping of liquids in petroleum and petrochemical processes. The invention is particularly valuable in mitigating high pumping-energy use in a simulated-moving-bed adsorption process.

A broad embodiment of the invention comprises a process for controlling the flowrate of and conserving energy in pumping one or more circulating streams in a consistent-pressure process for the separation of an adsorbed compound from a feed stream comprising two or more chemical compounds by adsorptive separation in a simulated moving bed contained in one or more multi-bed adsorbent chambers comprising a plurality of access points, wherein a feed stream and a desorbent stream each are injected into and an extract stream comprising the adsorbed compound and a raffinate stream each are individually withdrawn from the one or more adsorbent chambers during a cycle of processing through shifting individual access points, in which the at least one circulating stream comprises varying proportions of feed, desorbent, extract and raffinate circulated through the one or more adsorbent chambers by pumping at a flowrate which varies during the cycle of processing by at least about 10%, comprising propelling one or more pumps which circulate the one or more circulating streams by connection of at least one pump to variable-speed driving means.

A more specific embodiment is a process for controlling the flowrate of and conserving energy in pumping one or more circulating streams in a consistent-pressure process for the separation of para-xylene from mixed $C_8$-aromatics by adsorptive separation in a simulated moving bed contained in one or more multi-bed adsorbent chambers comprising a plurality of access points, wherein the $C_8$-aromatics stream and a desorbent stream each are injected into and an extract stream comprising para-xylene and a raffinate stream each are individually withdrawn from the one or more adsorbent chambers during a cycle of processing through shifting individual access points, in which the least one circulating stream comprises varying proportions of mixed $C_8$-aromatics, desorbent, para-xylene and raffinate circulated through the one or more adsorbent chambers by pumping at a flowrate which varies during a cycle of the processing by at least about 10%, comprising propelling one or more pumps which circulate the circulating streams by connection of at least one pump to variable-speed driving means.

A yet more specific embodiment is a process for controlling flowrate and conserving energy in pumping one or more circulating streams in a consistent-pressure process for the separation of para-xylene from mixed $C_8$-aromatics by adsorptive separation in a simulated moving bed contained in one or more multi-bed adsorbent chambers comprising a plurality of access points, wherein the $C_8$-aromatics stream and a desorbent stream each are injected into and an extract stream comprising para-xylene and a raffinate stream each are individually withdrawn from the one or more adsorbent chambers during a cycle of processing through shifting individual access points, in which the least one circulating stream comprises varying proportions of mixed $C_8$-aromatics, desorbent, para-xylene and raffinate circulated through the one or more adsorbent chambers by pumping at a flowrate which varies during a cycle of the processing by at least about 10%, comprising propelling one or more pumps which circulate the circulating streams by connection of at least one pump to variable-speed driving means; and controlling the timing of the pump and valve utilizing an algorithm of predictive load control to manipulate the speed of the variable-speed driven pump and adjust the position of the control concurrent with the indexing of the rotary valve to obtain proper inter-chamber fluid flow rates.

DETAILED DESCRIPTION OF THE INVENTION

As mentioned above, the present invention provides energy savings which are particularly relevant in variable-rate pumping of liquids in petroleum and petrochemical processes. When the flowrate of a pumped liquid stream varies during a cycle of processing by at least about 10%, and especially by about 25% or more, the pressure drop and related energy loss across the flow-controlling valve can have a substantial effect on processing costs. Energy may be conserved by employing variable-speed driving means for pumps circulating the liquid stream in the cycle of processing.

The invention may be applied usefully in one or more cycles of processing in separation processes. It is particularly useful in adsorptive separation in which large volumes of liquids are circulated at variable rates and consistent pressure through adsorption columns within the process. Control valves to control such liquid flows encounter large pressure drops particularly at relatively low flow rates. The cycle of processing is a consistent-pressure system, as measured at the base of columns of adsorbent, in that pressure is not deliberately varied during the cycle of processing although small variations of about 0.2 to 0.5, and preferably about 0.1 to 0.2 MPa, may occur incidental to process objectives.

Figure 1:
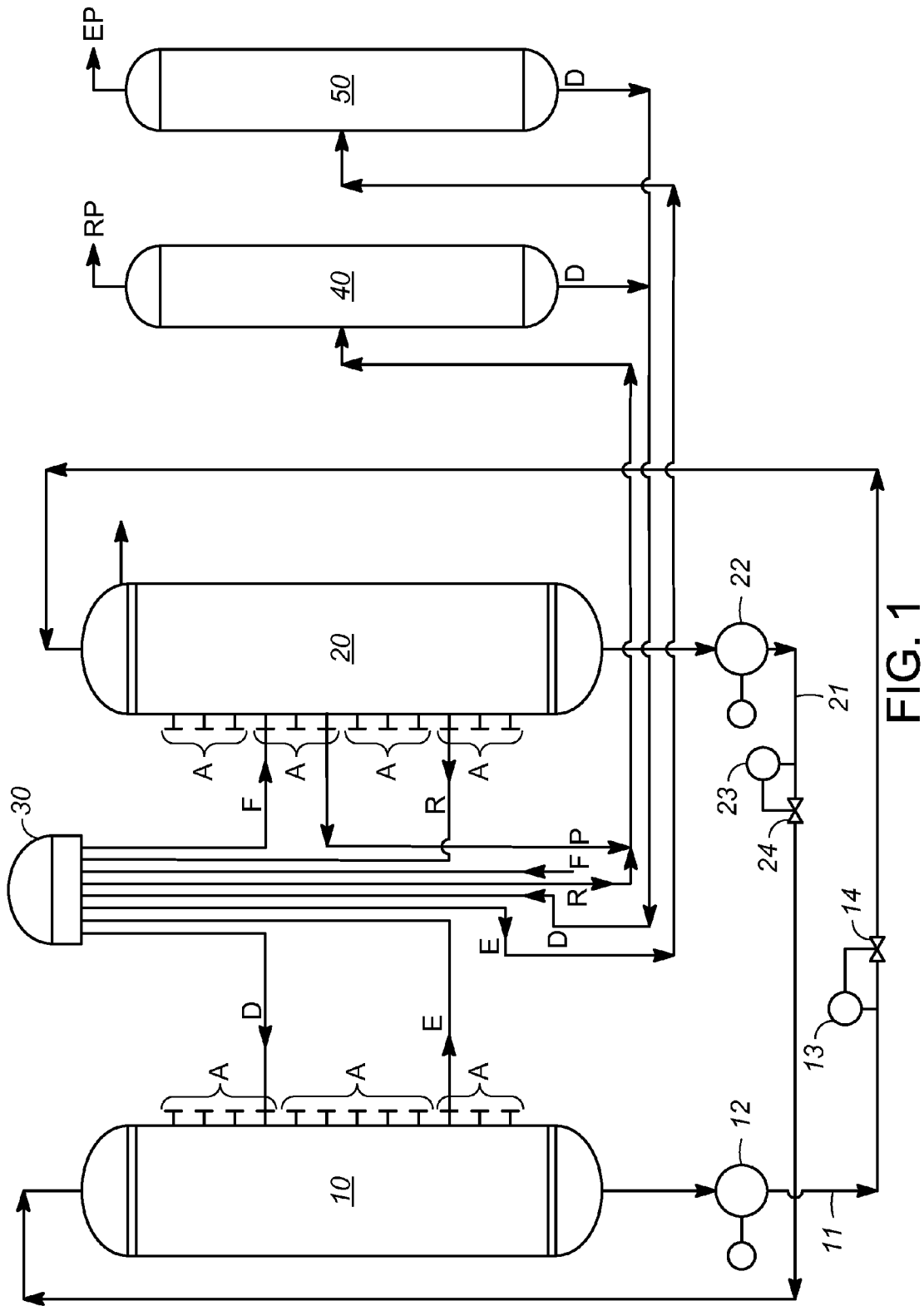
FIG. 1 is a schematic drawing of a conventional simulated-moving bed adsorption process for the recovery of para-xylene from mixed $C_8$ aromatics.

FIG. 1 illustrates the known art in the context of a process for the recovery of para-xylene from mixed $C_8$ aromatics using a solid adsorbent in the form of a simulated moving bed. The bed of solid adsorbent is held stationary and may be contained in two or more chambers 10 and 20. The adsorbent bed itself is usually a succession of fixed sub-beds. The locations at which various streams enter and leave the bed are periodically moved via access points A. The shift in the locations of liquid input and output in the direction of the fluid flow through the bed simulates the movement of the solid adsorbent in the opposite direction. The shift in locations of liquid input and output is accomplished by a fluid directing device 30 known generally as a rotary valve which works in conjunction with distributors located between the adsorbent sub-beds. The rotary valve accomplishes moving the input and output locations to specific distributors via access points A located between the adsorbent sub-beds. After a specified time period, called the step time, the rotary valve advances one index and redirects the liquid inputs and outputs to the distributors immediately adjacent and downstream of the previously used distributors.

The principal liquid inputs and outputs of the adsorbent system consist of four streams: the feed F, the extract E, the raffinate R, and the desorbent D. Each stream flows into or out of the adsorbent system at a particular flow rate, and each flow rate is independently controlled. The feed, when recovering para-xylene from a mixture of $C_8$ aromatics, comprises a mixture of xylenes and ethylbenzene along with small amounts of non-aromatic hydrocarbons. The desorbent introduced to the adsorbent system comprises a liquid capable of displacing feed components from the adsorbent. The extract, which is withdrawn from the adsorbent system, contains the separated para-xylene which was selectively adsorbed by the adsorbent along with desorbent. The raffinate, which is withdrawn from the adsorbent system, contains the other xylene isomers, ethylbenzene, and non-aromatic hydrocarbons which were less selectively absorbed by the adsorbent along with the desorbent.

There also may be associated flush streams P which purge distributors of inappropriate materials prior to shifting of access points. The streams pass from the adsorbent beds 10 and 20 to fractionators 40 and 50 for recovery of raffinate product RP and extract product EP, respectively, with recycle of desorbent D to the adsorbent chambers.

A circulating stream represented by 11 and 21 is conducted by pumps 12 and 22, respectively, which circulate liquid from the physical bottom of one adsorbent bed chamber to reenter the physical top of the other adsorbent bed chamber. The composition of the circulating stream, comprising feed, desorbent, extract and raffinate, changes with each valve step. As the four principal streams move through the adsorbent bed, not only the composition but also the volume of the combined stream entering and leaving the adsorbent bed varies significantly; the variation typically is as much as 60% when recovering para-xylene from mixed $C_8$ aromatics. The stream that conducts the effluent 11 from the physical bottom of the first chamber 10 via pump 12 to reenter the physical top of the second chamber 20 is considered as the pusharound stream, and the rate of this stream generally is controlled by a pressure controller 13 via valve 14. The stream conducting the effluent 21 from the physical bottom of the second chamber 20 to reenter the physical top of the first chamber 10 is considered as the pumparound stream and generally is controlled by a flow controller 23 and valve 24.

Figure 2:
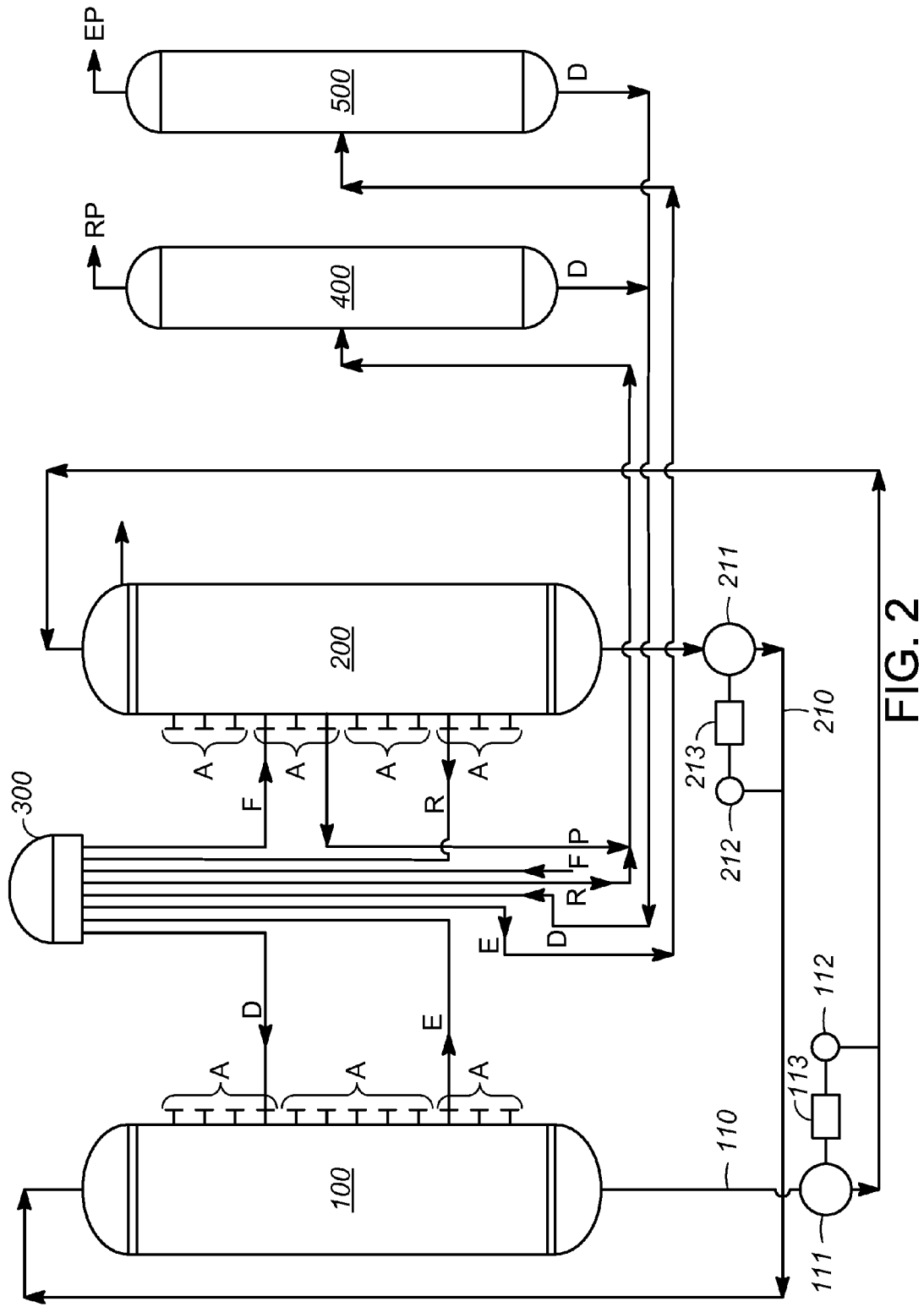
FIG. 2 is a schematic drawing of the FIG. 1 process showing the location of the energy-saving device of the present invention.
Figure 3:
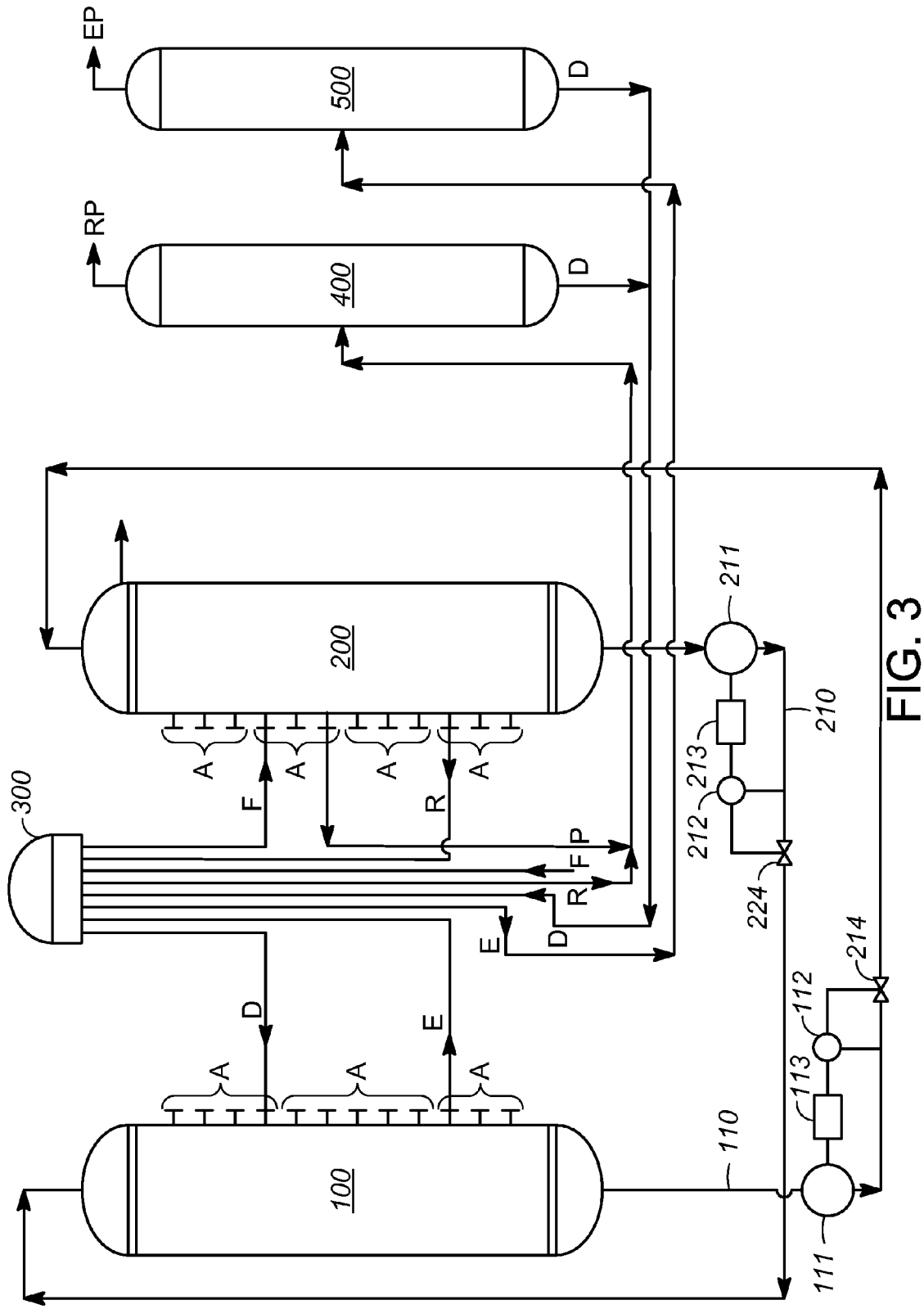
FIG. 3 is a schematic drawing of the FIG. 1 process showing an alternative arrangement u of the energy-saving device of the present invention.

FIGS. 2 and 3 show the placement in a continuous-adsorption process of the variable-speed driving means of the invention in the context of the process illustrated in FIG. 1. Adsorption chambers 100 and 200 correspond to chambers 10 and 20 of FIG. 1, rotary valve 300 corresponds to valve 30, and fractionators 400 and 500 correspond to the 40 and 50 of FIG. 1. Streams F, E, R and D have the same designation as in FIG. 1. Circulating streams 110 and 210 correspond to circulating streams 11 and 21 in FIG. 1.

To overcome such power losses, the present invention replaces control valves with variable-speed pumps and drivers as shown in FIGS. 2 and 3. These Figures duplicate the illustration of adsorbent beds 10 and 20 and rotary valve 30 of FIG. 1 with corresponding adsorbent beds 100 and 200 and rotary valve 300 as well as corresponding fractionators 400 and 500; descriptions of these correspond to the descriptions of FIG. 1 and are omitted for economy of description. The rates of pumparound stream 110 and 210 from adsorbent beds 100 and 200 are as indicated respectively in flow meters 112 and 212, which may be a turbine meter, external sensor or any other device known in the art to be capable of providing such flow rates. Circulating pumps 111 and 211 are positioned identically to pumps 12 and 22 of FIG. 1, but the FIG. 2 and FIG. 3 pumps are propelled by variable-speed drivers at flow rates indicated via meters 112 and 212 and control systems 113 and 213. The drivers may be configured, e.g., as a direct drive or gear-motor chain drive or any connection optimum for pump performance, and preferably is a direct drive to a centrifugal pump. The drivers may be motors having speed controlled be by varying one or more of the frequency or voltage to a motor; preferably, an induction motors are connected to centrifugal pumps with speed controlled by changing the frequency of an alternating-current voltage supply. Alternatively, the drivers may be continuously variable steam turbines as known in the art.

FIG. 3 differs from FIG. 2 with respect to the instrumentation and valving connected to the controllers 113 and 213. Rather than a flow indicator, FIG. 3 connects flow-control valves 214 and 224 to the controllers 113 and 213; when flow rates are increasing pump speed increases first, closing the CV and then upon transition of the net stream the CV opens, and when flows are decreasing CV closes first and after net stream transition occurs pump speed is decreased to open the valve. This use of control valves in conjunction with the variable-speed drivers and predictive load control reduces the size of the drivers and can smooth transition times from flow variations.

The variable-speed drivers preferably are controlled to conserve energy by an expert system which may comprise programmable logic controllers (PLCs), computer hardware, computer software, desktop computers, mainframe computers, servers, clients, integrated circuits, or other appropriate devices, either as separate elements or a single device in one location on or outside the system. The control system of the present invention serve to smooth the flow of circulating streams in an adsorption process preferably through an algorithm of predictive load control which utilizes not only measured flow data but also known parameters of the adsorption process and internal mathematical relationships. The algorithm used can usefully be termed a zone transition control algorithm (ZTC). The volume of the circulating stream changes in a known manner as input and output "zones" move through the adsorbent bed as determined by the indexed positions of the rotary valve to achieve appropriate fluid flow rates within the adsorbent bed. A particularly significant change in flows occurs as the raffinate transitions between chambers 100 and 200. These changes are programmed into the algorithm with adjustments to driver speeds and/or control valves anticipating the change before actual flow data are received; i.e., the algorithm senses controller positions during bed transitions in connection with the indexing of the rotary valve and subsequently prepositions the speed of a variable-speed motor and the optional control valve in relation to the indexing of the rotary valve to smooth oscillations, Further, the algorithm can sense the precision of the prepositioning and adjust subsequent positioning. The system thus controls the timing of changes in pump speed and the optional valve utilizing an algorithm of predictive load control to manipulate the speed of the variable-speed driven pump and adjust the position of the control concurrent with the indexing of the rotary valve to obtain proper inter-chamber fluid flow rates.

The pumparound and pusharound pumps of the known art, moving substantial and varying quantities of material around the adsorbent chambers, are significant energy consumers. The significant variations in the relatively large circulating combined stream result in substantial inefficiencies in energy use in these circulating pumps, according to the known art, which must be oversized to accommodate maximum flow. At a low flow rate of 2000 cubic meters per hour, the pressure drop across the associated control valve could be 350 kPa with 200 kW of dissipated power. The present invention thus offers significant potential for energy savings.

EXAMPLE

The amount of wasted energy associated with valve control of flow rates by was calculated for a hypothetical adsorptive-separation process. The average circulation rate was set at 2000 m$^3$/hour, and the rate varied over the cycle from about 119% to about 75% of the average rate. From about 46.3% to about 63% of the energy required for the pump was wasted for control as the flow rate varied. With two adsorption trains, the wasted power amounted to 9700 MW-hours per year with a value of $630,000 at a power cost of $0.065 per kW-hour.

It must be emphasized that the above description is merely illustrative of a preferred embodiment, and is not intended as an undue limitation on the generally broad scope of the invention. For example, the procedure for the simultaneous control of more than one characteristic can be readily extrapolated from the foregoing description. Similarly, one skilled in the art would understand how both the step time and the flow rates of the streams might be adjusted. While the description thus is narrow in scope, one skilled in the art will understand how to extrapolate to a broader scope of the invention.

The invention claimed is:

1. A process for controlling the flowrate of and conserving energy in pumping one or more circulating streams in a consistent-pressure process for the separation of an adsorbed compound from a feed stream comprising two or more chemical compounds by adsorptive separation in a simulated moving bed contained in one or more multi-bed adsorbent chambers comprising a plurality of access points, wherein a feed stream and a desorbent stream each are injected into and an extract stream comprising the adsorbed compound and a raffinate stream each are individually withdrawn from the one or more adsorbent chambers during a cycle of processing through shifting individual access points, in which the at least one circulating stream comprises varying proportions of feed, desorbent, extract and raffinate circulated through the one or more adsorbent chambers by pumping at a flowrate which varies during the cycle of processing by at least about 10%, comprising propelling one or more variable-speed pumps which circulate the one or more circulating streams by connection of at least one variable-speed pump to variable-speed driving means, and further comprising manipulating the speed of the variable-speed pump utilizing an algorithm of predictive load control, wherein the algorithm of predictive load control anticipates changes in the flowrate before receiving actual flowrate data during bed transitions within the one or more multi-bed adsorbent chambers in connection with indexing of a rotary valve, used for shifting the individual access points, to pre-position the speed of the variable speed pump.

2. The process of claim 1 wherein each of the variable-speed driving means consists of a variable-speed motor.

3. The process of claim 1 wherein the variable-speed driving means is a variable-speed steam turbine.

4. The process of claim 1 wherein the flowrate varies by about 25% or more.

5. The process of claim 1 wherein the feed stream comprises mixed $C_8$ aromatics and the extract stream comprises para-xylene.

6. The process of claim 1 wherein the feed stream comprises mixed $C_8$ aromatics and the extract stream comprises meta-xylene.

7. The process of claim 1 wherein the feed stream comprises a mixture of aliphatic and aromatic hydrocarbons and the extract stream comprises normal paraffins.

8. The process of claim 1 wherein the feed stream comprises a mixture of paraffinic and olefinic hydrocarbons and the extract stream comprises normal olefins.

9. A process for controlling the flowrate of and conserving energy in pumping one or more circulating streams in a consistent-pressure process for the separation of para-xylene from mixed $C_8$-aromatics by adsorptive separation in a simulated moving bed contained in one or more multi-bed adsorbent chambers comprising a plurality of access points, wherein the $C_8$-aromatics stream and a desorbent stream each are injected into and an extract stream comprising para-xylene and a raffinate stream each are individually withdrawn from the one or more adsorbent chambers during a cycle of processing through shifting individual access points, in which the least one circulating stream comprises varying proportions of mixed $C_8$-aromatics, desorbent, para-xylene and raffinate circulated through the one or more adsorbent chambers by pumping at a flowrate which varies during a cycle of the processing by at least about 10%, comprising changing the pump speed of one or more pumps which circulate the circulating streams by connection of at least one pump to variable-speed driving means, and wherein changing the pump speed comprises manipulating the pump speed of the variable-speed driven pump utilizing an algorithm of predictive load control, wherein the algorithm of predictive load control anticipates changes in the flowrate before receiving actual flowrate data during bed transitions within the one or more multi-bed adsorbent chambers in connection with indexing of a rotary valve, used for shifting the individual access points, to pre-position the speed of the variable-speed driven pump.

10. The process of claim 9 wherein each of the variable-speed driving means consists of a variable-speed motor.

11. The process of claim 9 wherein the variable-speed driving means is a variable-speed steam turbine.

12. The process of claim 9 wherein the flowrate varies by about 25% or more.

13. A process for controlling flowrate and conserving energy in pumping one or more circulating streams in a consistent-pressure process for the separation of para-xylene from mixed $C_8$-aromatics by adsorptive separation in a simulated moving bed contained in one or more multi-bed adsorbent chambers comprising a plurality of access points, wherein the $C_8$-aromatics stream and a desorbent stream each are injected into and an extract stream comprising para-xylene and a raffinate stream each are individually withdrawn from the one or more adsorbent chambers during a cycle of processing through shifting individual access points utilizing a rotary valve, in which the least one circulating stream comprises varying proportions of mixed $C_8$-aromatics, desorbent, para-xylene and raffinate circulated through the one or more adsorbent chambers by pumping at a flowrate which varies during a cycle of the processing by at least about 10%, comprising propelling one or more pumps which circulate the circulating streams by connection of at least one pump to variable-speed driving means; and controlling the timing of changes in pump speed utilizing an algorithm of predictive load control to manipulate the speed of the variable-speed driven pump and adjust the position of the control concurrent with the indexing of the rotary valve to obtain proper inter-chamber fluid flow rates, wherein the algorithm of predictive load control anticipates changes in the flowrate before receiving actual flowrate data during bed transitions within the one or more multi-bed adsorbent chambers in connection with indexing of the rotary valve.

14. The process of claim 13 further comprising utilizing the algorithm to change the position of a control valve.

15. The process of claim 13 wherein the at least one circulation stream comprises one or more pumparound streams and one or more pusharound streams.

16. The process of claim 13 wherein each of the variable-speed driving means consists of a variable-speed motor.

17. The process of claim 13 wherein the variable-speed driving means is a variable-speed steam turbine.

18. The process of claim 13 wherein the flowrate varies by about 25% or more.

* * * * *